(12) United States Patent
Stenzel

(10) Patent No.: US 7,524,527 B2
(45) Date of Patent: Apr. 28, 2009

(54) ELECTROSTATIC COATING OF A DEVICE

(75) Inventor: Eric B. Stenzel, Tuam (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 733 days.

(21) Appl. No.: 10/440,141

(22) Filed: May 19, 2003

(65) Prior Publication Data

US 2004/0234748 A1 Nov. 25, 2004

(51) Int. Cl.
*B05D 1/34* (2006.01)
*B05D 1/04* (2006.01)
*A61L 27/00* (2006.01)

(52) U.S. Cl. ............ 427/2.28; 427/2.24; 427/336; 427/475; 427/483; 427/486

(58) Field of Classification Search ............ 427/2.1, 427/2.2, 162, 475, 249, 335; 623/1.15, 1.39, 623/1.44
See application file for complete search history.

(56) References Cited

U.S. PATENT DOCUMENTS

| | | | |
|---|---|---|---|
| 5,279,863 A | | 1/1994 | Escallon |
| 5,836,925 A | * | 11/1998 | Soltesz ............ 604/525 |
| 6,120,847 A | * | 9/2000 | Yang et al. ............ 427/335 |
| 6,139,639 A | * | 10/2000 | Kitamura et al. ............ 118/680 |
| 6,368,658 B1 | | 4/2002 | Schwarz et al. |
| 6,749,902 B2 | * | 6/2004 | Yonker et al. ............ 427/458 |
| 2002/0172829 A1 | * | 11/2002 | Mori et al. ............ 428/407 |
| 2003/0054716 A1 | * | 3/2003 | Chou et al. ............ 442/110 |
| 2003/0134052 A1 | * | 7/2003 | Dave ............ 427/458 |
| 2003/0203000 A1 | * | 10/2003 | Schwarz et al. ............ 424/423 |
| 2004/0249437 A1 | | 12/2004 | Sundar |
| 2006/0165872 A1 | * | 7/2006 | Chappa et al. ............ 427/2.24 |

FOREIGN PATENT DOCUMENTS

| | | |
|---|---|---|
| EP | 0 086 847 | 10/1986 |
| WO | WO 02/26281 A1 | 4/2002 |
| WO | WO 03/024497 A1 | 3/2003 |
| WO | WO 03/082363 A | 10/2003 |
| WO | WO 03/090806 A | 11/2003 |
| WO | WO 2004/014453 | 2/2004 |
| WO | WO 2004/028407 A1 | 4/2004 |
| WO | WO 2004/103428 A | 12/2004 |

OTHER PUBLICATIONS

Powder Coating The Complete Finishers Handbook, first edition, 1994, pp. 12-13.*
Encyclopedia of Chemical Technology, 1994, V.8, p. 514-515.*
Encyclopedia of Polymer Science and Engineering, 2$^{nd}$ ED., 1987, p. 191.*

* cited by examiner

*Primary Examiner*—Frederick J Parker
(74) *Attorney, Agent, or Firm*—Kenyon & Kenyon

(57) ABSTRACT

The present invention concerns bio-compatible medical devices and process for preparation thereof. The process includes electrostatically forming a first layer on a structure. The first layer can include a combination of at least one active substance and at least one polymer and/or binder. A second layer is formed on the structure to cover the first layer. The second layer can be a solvent or a combination of solvents. The evaporation of the second layer causes the first layer to reflow and bind to the structure.

15 Claims, 1 Drawing Sheet

ELECTROSTATIC COATING OF A DEVICE

TECHNICAL FIELD

The present invention relates to the controlled delivery of therapeutic agents to a target site of an organic vessel.

BACKGROUND

Medical implants are used for a number of medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Such localized delivery of therapeutic agents has been achieved using medical implants which both support a lumen within a patient's body and place appropriate coatings containing absorbable therapeutic agents at the implant location. Examples of such medical devices include catheters, guide wires, balloons, filters (e.g., vena cava filters), stents, stent grafts, vascular grafts, intraluminal paving systems, implants and other devices used in connection with drug-loaded polymer coatings. Such medical devices are implanted or otherwise utilized in body lumina and organs such as the coronary vasculature, esophagus, trachea, colon, biliary tract, urinary tract, prostate, brain, and the like.

The process of applying a coating onto a stent may be accomplished by a number of methods including spray coating, spin-coating, and electrostatic deposition. The spray-coating method has been frequently used because of its excellent features, e.g., good efficiency and control over the amount or thickness of coating. However, the conventional spray-coating methods, which are usually implemented with a device such as an airbrush, have drawbacks. For example, when a medical device has a structure such that a portion of the device obstructs sprayed droplets from reaching another portion of the device, then the coating becomes uneven. Specifically, when a spray-coating is employed to coat a stent having a tube-like structure with openings, such as stents described in U.S. Pat. Nos. 4,655,771 and 4,954,126 to Wallsten, the coating on the inner wall of the tube-like structure tends to be thinner than that applied to the outer wall of the tube-like structure. Hence, conventional spraying methods tend to produce coated stents with coatings that are not uniform. Furthermore, conventional spraying methods are inefficient. In particular, generally only 5% of the coating solution that is sprayed to coat the medical device is actually deposited on the surface of the medical device. The majority of the sprayed coating solution is therefore wasted.

In the so-called spin-dipping process, a medical device is coupled to a spinning device, and then, while rotating about a central axis, the medical device is dipped into a coating solution to achieve the desired coating. This process also suffers from many inefficiencies including the unevenness of the coated layer and a lack of control over the coated layer's thickness.

In addition to the spray coating and spin-dipping methods, the electrostatic deposition method has been suggested for coating medical devices. For example, U.S. Pat. Nos. 5,824,049 and 6,096,070 to Ragheb et al. mention the use of electrostatic deposition to coat a medical device with a bioactive material. In the conventional electrodeposition or electrostatic spraying method, a surface of the medical device is grounded and a gas may be used to atomize the coating solution into droplets. The droplets are then electrically charged using, for example, corona discharge, i.e., the atomized droplets are electrically charged by passing through a corona field. Since the droplets are charged, when they are applied to the surface of the medical device, they will be attracted to the surface since it is grounded.

One disadvantage of conventional electrostatic spraying is that it requires a complicated spraying apparatus. In addition, because the conventional electrostatic systems use a gas to move the droplets from a source to a target, controlling the gas pressure is crucial for accurate coating. However, it is not easy to control the gas pressure so that the target surface is evenly and sufficiently coated without losing much of the coating solution.

Therefore, there is a need for an improved method for coating medical devices that provides even and uniform coatings over the entire surface that is to be coated. Each of the references cited herein is incorporated by reference herein for background information.

SUMMARY OF THE INVENTION

The present invention concerns methods and apparatus for providing a substantially uniform coating on a structure. In one embodiment, the present invention is directed to a medical device adapted for insertion into a body lumen wherein the medical device is coated with an active substance and a bio-compatible polymer for binding the active substance to the structure.

In a process according to one embodiment of the invention, a method for coating a medical device includes forming a first coating on a bio-compatible structure by electrostatically depositing an active substance and a polymer on the structure, forming a second coating on the structure by depositing a solvent to at least partially cover the first coating, and causing a reflow of the first coating by evaporating the solvent from the structure. The polymer can be a binder or a resin or any material that can bind the active substance on the structure.

In a process according to another embodiment of the invention, a medical device is coated by forming a first layer of an active substance on a structure, forming a second coating to at least partially cover the first coating, the second coating having a bio-compatible polymer, and exposing at least one of the first or the second coating to a solvent to cause a re-flow the polymer. The step of forming a first coating on the structure can include grinding and/or milling the active substance into a fine powder and electrostatically charging and depositing the powder on the structure using the electrostatic charge difference between the active substance and the structure.

DETAILED DESCRIPTION OF THE INVENTION

Figure 2:
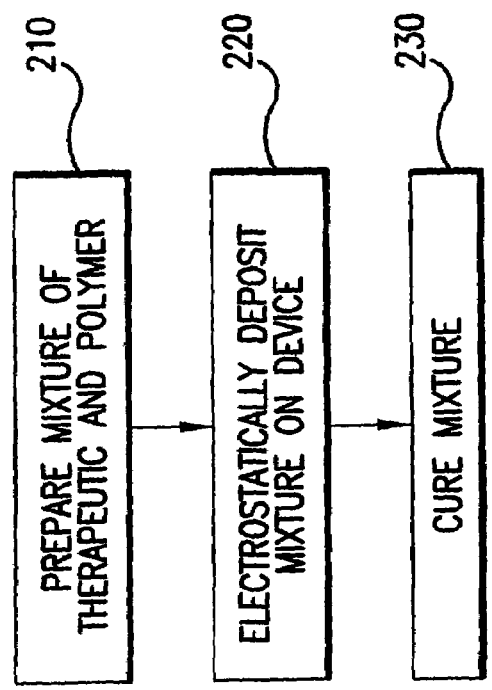
FIG. 2 illustrates general categories of steps that may be undertaken to carry out the invention, in accordance with details described below.

As used herein, the term "therapeutic agent" includes one or more "therapeutic agents" or "drugs". The terms "therapeutic agents", "active substance" and "drugs" are used interchangeably herein and include pharmaceutically active compounds, nucleic acids with and without carrier vectors such as lipids, compacting agents (such as histones), virus (such as adenovirus, andenoassociated virus, retrovirus, lentivirus and α-virus), polymers, hyaluronic acid, proteins, cells and the like, with or without targeting sequences.

In one embodiment of the invention, a process for coating a structure such as a stent includes first preparing a mixture of a polymer and an active substance or therapeutic. The mixture may be in the form of a powder. Then, the process includes forming a first coating on the structure by electrostatically depositing the mixture on the structure. This step can be followed by a step to cure the mixture.

One way to cure the mixture includes forming a second coating to at least partially cover the first layer. The second coating can include a solvent. If a second coating including a solvent is deposited, the coating can be applied such that at least portions of the first coating are covered by the solvent. The solvent can be evaporated to enable the reflow of the first coating. Alternatively, the second coating of one or more solvents is formed on, and is absorbed by, the first coating to cause coating reflow. The solvents can be evaporated from the device by using infrared drying, laser drying, convection of hot air or vacuum ovens.

In an alternative embodiment, the mixture can be cured by heating the powder covered stent to melt the first coating, causing it to flow. This can be used with or without a second coating.

The step of forming a first coating or the first layer on the structure can be implemented in accordance with one of several methods. In one embodiment of the invention, the first coating is deposited and the first layer is formed on the structure through electrostatic deposition. According to this embodiment, a mixture containing the desired ratio of an active substance and one or more polymers is prepared. The active substance and the polymer can be ground and/or milled to form a fine powder. The active substance(s) and/or the polymer can be chilled as desired to freeze the material into a solid to enhance the process of forming a powder through grinding or milling. While powder size of any suitable range can be used, in one embodiment, the polymer and the active substance are milled to form a fine powder in the range of 0.0001-0.025 mm.

If the polymer or the active substance is a liquid at room temperature, it can be frozen with liquid nitrogen or other suitable freezing method to assume a solid phase. Once the mixture or one of the ingredients has been prepared in the frozen state, it can be ground and deposited in the frozen state. The electrostatic coating system can comprise any conventional coating system that uses electrostatic deposition principles.

In another embodiment, the invention defines a process for coating a medical device, the process including forming a first layer on a structure where the first layer includes an active substance; forming a second layer on the structure where the second layer includes a bio-compatible polymer; exposing at least one of the first or the second layers to a solvent to re-flow the active substance; and drying the structure. The step of forming a first layer on the structure can further include grinding the active substance into a fine powder, electrostatically charging the fine powder, discharging the structure to substantially free the structure from electrostatic charge and depositing the fine powder on the structure. A medical device coated in this manner can be inserted into a body lumen.

In one embodiment of the invention, the powder is passed through an electromagnetic field (e.g., corona discharge) having a flux density for charging the powder particles. Once the particles are charged, they can be directed toward the structure. The structure can be grounded so as to have no charge. Alternatively, the structure can be charged to have an opposite charge to that of the powder particles. In either case, the attraction between the charges particles and the grounded structure will draw the particles to the structure. Once the powder particles are placed near the structure, the electromagnetic field will transport the powder particles on to the structure. As charged powder particles are deposited on the surface of the structure, a coating is formed. The areas not covered by the coating will retain their greater attraction for the charged particles. During the coating process, the charged particles will seek out the greatest attractive force. At the start of the powder coating process, the greatest force is associated with the bare metal frame; hence this area will coat first. As a result, the newly introduced particles will be drawn to areas that have not been coated. As the bare metal areas become covered in the powder mixture, the next most attractive surface would be the thinnest coated area on the device. This provides for an even coating of the device. Thus, a coating layer of substantially uniform thickness will form throughout the surface of the structure.

Additional steps can be taken to ensure that the desired amounts of the active substance and/or the polymer have been deposited. For example, the structure can be coupled to a fine scale that monitors the weight of any additional coating deposited thereon. In this embodiment, the electrostatic deposition process continues until the stent and the coating reach the desired weight.

In one embodiment of the invention, the first layer comprises either a binder or an active substance. According to this embodiment, once the first layer has been deposited, a second layer can be deposited to include the missing ingredient(s). The second layer can include one or more solvents.

Once the combination of an active substance and one or more polymers have been deposited to form a coating, a reflow of the coating can be initiated. Reflow can be initiated by heating the structure with the coating(s) thereon to cause melting of the coating(s). For example, the structure can be placed in an oven or a heated chamber to melt the polymer coating and cause reflow thereof. Once the polymer coating is melted it reflows to cover the surface of the structure. In an embodiment where the structure is a stent, the reflow will enable the coating to substantially cover the struts.

Reflow can also be initiated by adding a coating one or more solvents. The solvent may be sprayed on the coated stent to cause the polymer to reflow. In another embodiment, solvent can be electrostatically charged and then deposited on the structure to at least partially cover any existing coating(s). Suitable solvents that can be sprayed or electrostatically deposited on the structure include tetra hydro furan (THF), chloroform, toluene, methyl ethyl keton (MEK) and any other solvent that may be sprayed or electrostatically deposited. In another exemplary embodiment, solvent is added by dipping the structure into the solvent.

In still another exemplary embodiment, the pre-coated structure is placed in a chamber having a high vapor pressure of a solvent at a first temperature. A pre-coated device at a second temperature that is lower than the first temperature is lowered into solvent vapor. The solvent vapor will condense on the cooler pre-coated device thus transferring solvent to the pre-coated device causing the polymer to absorb the solvent and reflow to form the coated layer. It will be understood that departure from the exemplary embodiments enumerated herein is still considered to be within the scope of the invention to the extent that the principles of the invention have been utilized.

The coating material can comprise an active substance in a polymer matrix. According to one embodiment, an active substance is dissolved in a polymer solution to form a liquid mixture. The liquid mixture can be crystalized by any of the conventional methods to form a powder. A preferred method of crystallizing the mixture would be to freeze it. Next, the powder is ground to a size suitable for electrostatic deposition and deposited on the structure.

Curing the mixture can occur in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

In a preferred embodiment, the polymer used to coat the medical device is provided in the form of a coating on an expandable portion of a medical device. After applying the drug solution to the polymer and evaporating the volatile solvent from the polymer, the medical device is inserted into a body lumen where it is positioned to a target location. In the case of a balloon catheter, the expandable portion of the catheter can be subsequently expanded to bring the drug-impregnated polymer coating into contact with the lumen wall. The drug is released from the polymer as it slowly dissolves into the aqueous bodily fluids and diffuses out of the polymer. This enables administration of the drug to be site-specific, limiting the exposure of the rest of the body to the drug.

Figure 1:
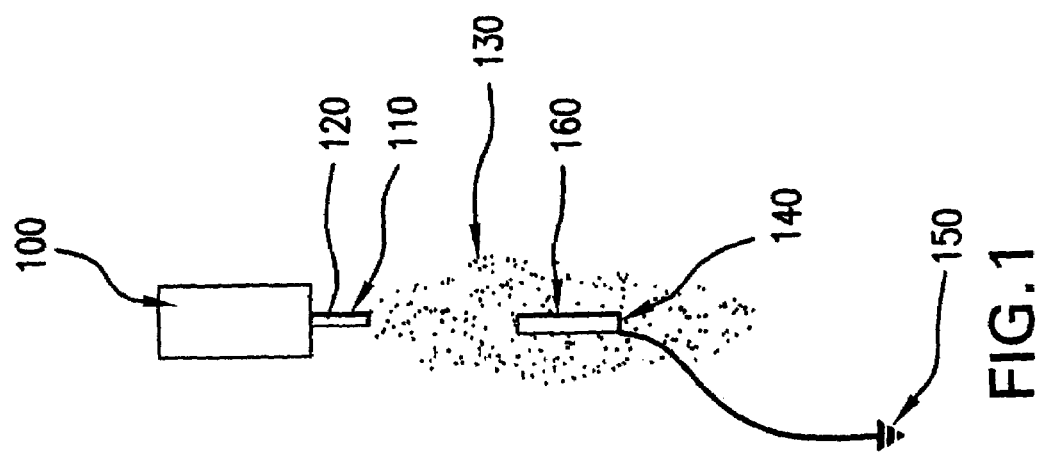
FIG. 1 is a schematic representation of one embodiment of the invention.

FIG. 1 is a schematic representation of one embodiment of the invention. FIG. 1 shows powder application unit 100 that pumps the powder through conductive charging nozzle 110. Depending on the application, the powder application unit may need to be cooled to retain the powder in a solid state. In the embodiment of FIG. 1, high voltage power source 120 is connected to the conductive charging nozzle 110 to provide electrostatic charge thereto. Charged powder stream 130 exits the nozzle and is immediately repelled from similarly-charged particles. This causes the charged particle stream to disperse as a cloud. The device to be coated, in this case stent 160 can be placed in the proximity of charging nozzle 110. As shown in FIG. 1, stent 160 is grounded through wire 140 to ground point 150. Ground point 150 need not be an absolute grounding point. Rather, it is sufficient that ground point 150 have zero potential with respect to high voltage source 120, thus causing electrostatic attraction of charged powder stream 130 (now dispersed into a charged powder cloud) to stent 160.

FIG. 2 illustrates general categories of steps that may be undertaken to carry out the invention, in accordance with details described below. Referring to FIG. 2, a mixture of therapeutic and polymer material is prepared at step 210. The mixture is then electrostatically deposited on the device that is to be coated at step 220. Finally, the coated mixture is cured at step 230.

The polymer used in the present invention is preferably capable of absorbing or retaining a substantial amount of drug solution. When applied as a coating on a medical device in accordance with the present invention, the dry polymer is typically on the order of about 1 to about 50 microns thick. In the case of a balloon catheter, the thickness is preferably about 1 to 10 microns thick, and more preferably about 2 to 5 microns. Very thin polymer coatings, e.g., about 0.2-0.3 microns and much thicker coatings, e.g., more than 10 microns, are also possible. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collage and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

Specific examples of therapeutic agents used in conjunction with the present invention include, for example, pharmaceutically active compounds such as paclitaxel, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/antimitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor", platelet-derived endothelial growth factor, platelet-derived growth factor, tumor necrosis factor, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5; BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

In an exemplary embodiment of the invention, a first coating can be prepared by preparing a fine powder mixture of paclitexal and one or more polymer; alternatively, the mixture can include a mixture of a polymer, paclitaxel and a solvent. The mixture can be grinded and charged to have an electrostatic charge. The charged mixture can be deposited on a structure using the appropriate electrostatic deposition equipment. To enhance deposition, the structure can be grounded. In addition, the structure can be connected to a micro-scale that monitors the weight of the deposited coating. Thereafter, the structure having one layer of coating can be placed in a chamber that has a high vapor pressure of the solvent present. The presence of solvent and its deposition on the coating can initiate the reflow process. Optionally, after the electrostatic process is completed, air brush or other means can be used to remove any loose particles or coating.

It is envisioned that the above method may be utilized wherein the first coating does not include a solvent. Alternatively a solver/polymer/therapeutic mixture can be prepared, then frozen solid, then ground as a powder, and then electrostatically deposited. When the coating melts, the coating will reflow.

It will be recognized by one of ordinary skill in the art that the embodiments and examples described and illustrated herein are merely illustrative, as numerous other embodiments or permutations thereof may be implemented without departing from the spirit and scope of the present invention.

What is claimed is:

1. A process for coating a medical device comprising:
   forming a first coating on a bio-compatible structure by electrostatically depositing a mixture of a biologically active substance and a polymer on the structure;
   wherein the mixture flows onto the structure during the depositing step;
   after forming the first coating, applying a solvent to at least partially cover the first coating and to cause a flow of the first coating;
   wherein the step of applying the solvent comprises spraying the solvent to at least partially cover the first coating; and
   evaporating the solvent;
   wherein evaporating the solvent comprises at least one of infrared drying and laser drying after the first coating and the solvent have been deposited thereon.

2. The process of claim 1, wherein the polymer is a binder.

3. The process of claim 1, further comprising freezing the active substance to form a solid phase, grinding and/or milling the solid phase to form a frozen solid powder and mixing the frozen solid powder with the polymer to form the mixture of the active substance and the polymer.

4. The process of claim 3, where the polymer is frozen to a solid phase, ground to a powder and added to the active substance.

5. The process of claim 3, wherein the freezing step comprises freezing the active substance with liquid nitrogen.

6. The process of claim 1, wherein the step of forming a first coating comprises predetermining a desired amount of the first coating to be deposited, and monitoring a weight of the deposited first coating during deposition.

7. The process of claim 1, wherein the step of applying the solvent comprises electrostatically depositing the solvent to at least partially cover the first coating.

8. The process of claim 1, wherein the mixture of the active substance and the polymer is a powder mixture.

9. The process of claim 1, further comprising air brushing the structure to remove any debris.

10. The process of claim 1, wherein the mixture for forming the first coating is in the form of a solid powder when deposited on the structure.

11. A process for coating a medical device, the process comprising:
   electrostatically depositing a first material to form a first layer on a structure, the first material including an active substance;
   wherein the first material flows onto the structure during the depositing step;
   forming a second layer on the structure, the second layer including a bio-compatible polymer;
   applying a solvent to at least partially cover the first layer and second layer to cause a flow of the first layer; and
   evaporating the solvent;
   wherein evaporating the solvent comprises at least one of infrared drying and laser drying after the first layer, the second layer and the solvent have been deposited thereon.

12. The process of claim 11, wherein the step of forming a first layer on the structure comprises:
   grinding the active substance into a powder;
   electrostatically charging the powder;
   discharging the structure to substantially free the structure from electrostatic charge; and
   depositing the powder on the structure.

13. The process of claim 11, where the active substance includes a polymer.

14. The process of claim 13, where the active substance is frozen to a solid state to enhance grinding into a powder.

15. The process of claim 14, where the polymer is frozen to a solid state to enhance grinding into a powder.

* * * * *

UNITED STATES PATENT AND TRADEMARK OFFICE
CERTIFICATE OF CORRECTION

PATENT NO. : 7,524,527 B2
APPLICATION NO. : 10/440141
DATED : April 28, 2009
INVENTOR(S) : Eric B. Stenzel It is certified that error appears in the above-identified patent and that said Letters Patent is hereby corrected as shown below:

Column 2, line 64, "virus" should be changed to --viruses--;
Column 2, line 65, ""andenoassociated virus" should be changed to --adeno-associated virus--;
Column 4, line 39, "coating one" should be changed to --coating of one--;
Column 4, line 46, "methyl ethyl keton (MEK)" should be changed to --methyl ethyl ketone (MEK)--;
Column 6, line 23, "(BAYHDROL®, etc)" should be changed to --(BAYHYDROL®, etc)--;
Column 6, line 27, "collage" should be changed to --collagen--;
Column 6, lines 53-54, "viral, liposomes" should be changed to --viral liposomes--;
Column 7, line 10, "nitorfurantoin" should be changed to --nitrofurantoin--;
Column 7, line 12, "lisidomine" should be changed to --linsidomine--;
Column 7, line 19, "Warafin" should be changed to --warfarin--;
Column 7, line 21, "promotors" should be changed to --promoters--;
Column 7, line 23, "promotors" should be changed to --promoters--;
Column 7, line 31, "endogeneus vascoactive" should be changed to --endogenous vasoactive--;
Column 8, line 2, "("BMP's")" should be changed to --("BMPs")--;
Column 8, line 6, "BMP's" should be changed to --BMPs--;
Column 8, line 12, "DNA's" should be changed to --DNAs--; and
Column 8, line 15, "paclitexal" should be changed to --paclitaxel--.

Signed and Sealed this

Nineteenth Day of October, 2010

David J. Kappos
*Director of the United States Patent and Trademark Office*